(12) United States Patent
Escorcia et al.

(10) Patent No.: US 8,781,860 B2
(45) Date of Patent: Jul. 15, 2014

(54) OPTIMIZATION OF CHRONIC PAIN MANAGEMENT OVER A COMMUNICATIONS NETWORK

(76) Inventors: Alvaro Escorcia, Sugarland, TX (US);
Erica Escorcia, Miami, FL (US);
Alvaro Ramirez, Miami, FL (US)

(*) Notice: Subject to any disclaimer, the term of this patent is extended or adjusted under 35 U.S.C. 154(b) by 0 days.

(21) Appl. No.: 13/609,166

(22) Filed: Sep. 10, 2012

(65) Prior Publication Data
US 2014/0074491 A1  Mar. 13, 2014

(51) Int. Cl.
*G06Q 50/00* (2012.01)
*A63B 24/00* (2006.01)

(52) U.S. Cl.
CPC ......... *A63B 24/0075* (2013.01); *A63B 24/0062* (2013.01); *A61B 2505/09* (2013.01)
USPC .............. 705/3; 482/1; 482/8; 482/9; 700/17; 600/300; 434/247

(58) Field of Classification Search
CPC ........... A63B 24/0075; A63B 24/0062; A61B 2505/09
USPC ............ 705/3; 600/300; 434/247; 340/573.1; 700/17
See application file for complete search history.

(56) References Cited

U.S. PATENT DOCUMENTS

| 8,306,635 | B2* | 11/2012 | Pryor | 700/17 |
|---|---|---|---|---|
| 2002/0128864 | A1* | 9/2002 | Maus et al. | 705/2 |
| 2007/0156032 | A1* | 7/2007 | Gordon et al. | 600/300 |
| 2009/0047644 | A1* | 2/2009 | Mensah et al. | 434/247 |
| 2009/0219159 | A1* | 9/2009 | Morgenstern | 340/573.1 |
| 2009/0298650 | A1* | 12/2009 | Kutliroff | 482/8 |
| 2009/0312152 | A1* | 12/2009 | Kord | 482/9 |
| 2011/0034300 | A1* | 2/2011 | Hall | 482/1 |
| 2012/0139731 | A1* | 6/2012 | Razoumov et al. | 340/573.1 |

OTHER PUBLICATIONS

Google patents search results, Sep. 26, 2013.*

* cited by examiner

*Primary Examiner* — Dilek B Cobanoglu
(74) *Attorney, Agent, or Firm* — Mark Terry (57) ABSTRACT

A method for facilitating treatment of patients, wherein the server is communicatively coupled to a communications network, is provided that solves the above-described problems. The method includes receiving, via the communications network, an exercise regimen for a patient, wherein the exercise regimen includes a normalized model of at least one exercise activity, transmitting, via the communications network, the exercise regimen to a computing device of the patient, receiving, via the communications network, patient observation data, including a log of the patient performing the least one exercise activity, and generating a report including data from the exercise regimen and the patient observation data.

19 Claims, 6 Drawing Sheets

OPTIMIZATION OF CHRONIC PAIN MANAGEMENT OVER A COMMUNICATIONS NETWORK

CROSS-REFERENCE TO RELATED APPLICATIONS

This patent application claims priority to patent application Ser. No. 13/494,005, filed Jun. 11, 2012, and entitled "Optimization of Chronic Pain Management," which claims priority to provisional patent application No. 61/495,632, filed on Jun. 10, 2011 and entitled "Optimization of Chronic Pain Management." The subject matter of patent application Ser. No. 13/494,005 and patent application No. 61/495,632 is hereby incorporated by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The technical field relates generally to the field of healthcare and, more specifically, relates to the field of pain management over a communications network.

BACKGROUND

Pain is a silent epidemic in the United States. Tens of millions of Americans live with chronic pain caused by disease, disorder or accident. Additional millions suffer acute pain resulting from surgery or accident. A majority of these individuals in pain have been living with this affliction for multiple numbers of years. The loss of productivity and daily activity due to pain is substantial. Additionally, it has been estimated that millions of individuals see a physician for chronic pain treatment every year. Thus, our healthcare system is significantly affected by the amount of resources that are allocated to treat pain each year.

One common treatment for sufferers of chronic pain is physical therapy and/or exercise. Often, a physician will prescribe a physical therapy and/or exercise regimen to a chronic pain patient. A regimen includes performing certain exercises or movements for a predefined period of time, one or more times a week. In between visits to the physician, however, there is no currently available way of monitoring the patient's adherence to the regimen. That is, the physician cannot confirm that the patient was performing the exercises properly and at the right frequency in between office visits. Thus, when patient's return to see the physician, the doctor must rely on the patient's memory and the patient's ability to self-report, which may not be completely accurate. Therefore, a doctor providing pain management care today may not have a correct picture of the efficacy of certain physical therapy or exercise regimens on chronic pain sufferers.

To facilitate the provision of care to patients afflicted with pain, healthcare professionals often develop a risk profile of the patient that defines the risk of the patient further worsening his or her current affliction, developing additional sources of pain or having a recurrence of pain. Currently, however, there is no precise or automated way to generate a risk profile for patients experiencing pain. Further, there is no exhaustive risk profile generation process that takes multitudes of factors into account, such as demographic data of the patient. Another problem associated with the treatment of chronic pain is the ability to precisely define results or outcomes when monitoring and tracking a patient's progress. Because the perception of pain can be subjective and because various, and sometimes different, factors can be considered when evaluating the results of pain treatment, there is no generally-accepted paradigm for defining results precisely. In the medical field, this leads to a great disparity in how success or failure of a pain treatment plan is determined.

Therefore, what is needed is a system and method for improving upon the problems with the prior art, and more particularly for a more efficient and precise way of managing a patient's chronic pain over a communications network.

SUMMARY

A method for facilitating treatment of patients, wherein the server is communicatively coupled to a communications network, is provided. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a method for facilitating treatment of patients, wherein the server is communicatively coupled to a communications network, is provided that solves the above-described problems. The method includes receiving, via the communications network, an exercise regimen for a patient, wherein the exercise regimen includes a normalized model of at least one exercise activity, transmitting, via the communications network, the exercise regimen to a computing device of the patient, receiving, via the communications network, patient observation data, including a log of the patient performing the least one exercise activity, and generating a report including data from the exercise regimen and the patient observation data.

BRIEF DESCRIPTION OF THE DRAWINGS

The accompanying drawings, which are incorporated in and constitute a part of this disclosure, illustrate various example embodiments. In the drawings.

DETAILED DESCRIPTION

The following detailed description refers to the accompanying drawings. Wherever possible, the same reference numbers are used in the drawings and the following description to refer to the same or similar elements. While embodiments of the invention may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the invention. Instead, the proper scope of the invention is defined by the appended claims.

The present invention improves upon the problems with the prior art by providing a system and method for allowing a physician or other healthcare professional to confirm that a patient has been performing prescribed exercises properly and at the right frequency in between office visits. When a patient returns to see a physician or other healthcare professional for a follow up visit, the present invention provides highly accurate data regarding the current status of the patient, his or compliance with the prescribed regimen and the efficacy of the exercise regimen in treating the patient's affliction. Further, the present invention provides a precise and automated way to generate a risk profile for patients experiencing pain, wherein the risk profile takes multitudes of factors into account, such as demographic data of the patient. Also, the present invention precisely defines results or outcomes when monitoring and tracking a patient's progress in relation to an exercise regimen. Thus, the present invention allows a doctor providing pain management care to have a full and accurate picture of the efficacy of the physical therapy or exercise regimens on chronic pain sufferers.

Figure 1:
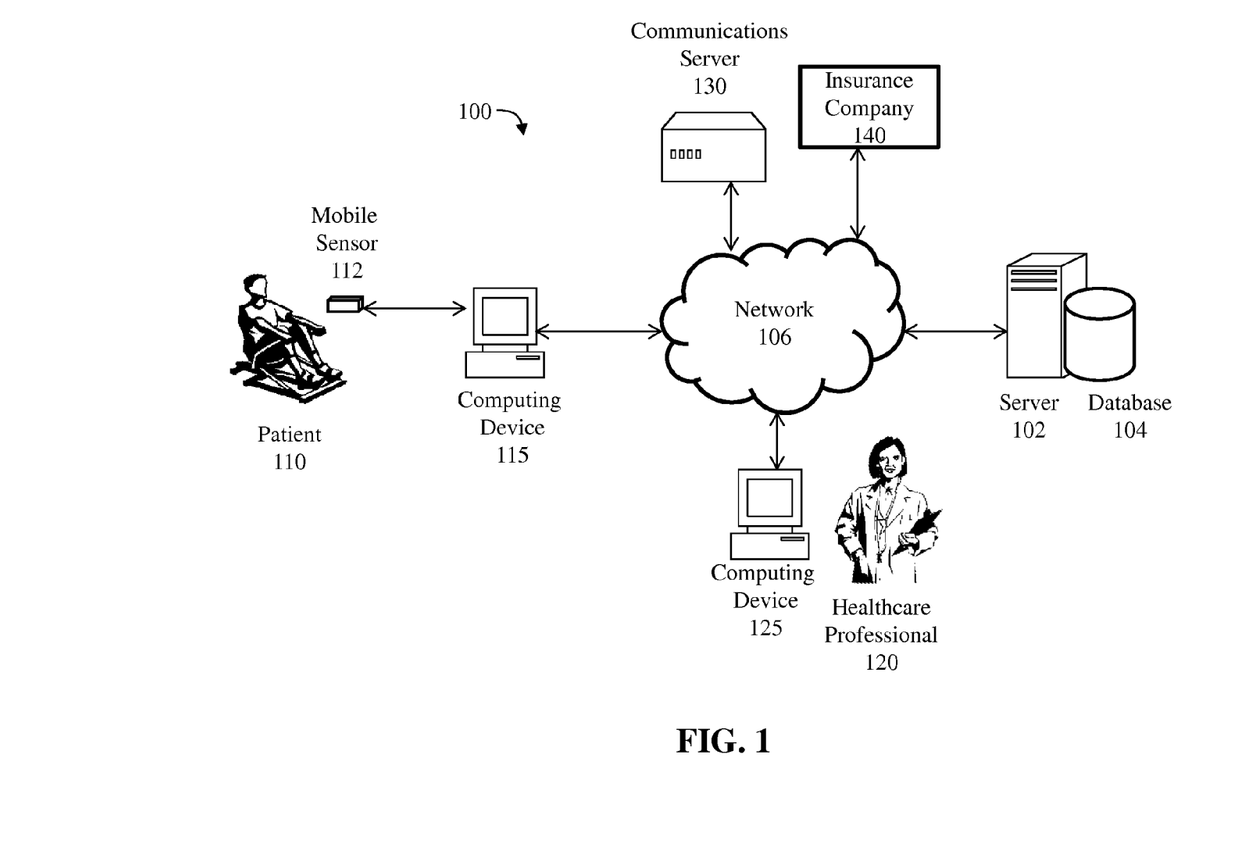
FIG. 1 is a block diagram of an operating environment that supports a process for facilitating treatment of patients via a server communicatively coupled with a communications network, according to an example embodiment.

FIG. 1 is a block diagram of an operating environment 100 that supports a process for facilitating treatment of patients via a server 102 communicatively coupled with a communications network 106, according to an example embodiment. The environment 100 may comprise at least two computing devices 115, 125 and a server 102 communicating via a communications network 106. The computing devices 115, 125 may be connected either wirelessly or in a wired or fiber optic form to the communications network 106. The environment 100 may further comprise at least one mobile activity sensor 112 communicatively coupled, either wirelessly or in a wired or fiber optic form to the computing device 115. Further, environment 100 includes communications server 130 coupled to network 106. Communications network 106 may be a packet switched network, such as the Internet, or any local area network, wide area network, enterprise private network, cellular network, phone network, mobile communications network, or any combination of the above.

Sensor 112 and computing devices 115, 125 may each comprise a computing device 600, described below in greater detail with respect to FIG. 6. In one embodiment, mobile activity sensor 112 may be a pedometer, accelerometer, GPS positioning device and/or any other personal and wearable sensor that records the activity of a patient 110, i.e., patient movement data. In another embodiment, mobile activity sensor 112 may include functions that record vital information of patient 110, such as blood pressure, heart rate, wattage output, pulse oximetry, skin conductance, breathing rate, i.e., patient vital data. Further, sensor 112 and computing devices 115, 125 may each comprise mobile computing devices such as cellular telephones, smart phones, tablet computers, or other computing devices such as a desktop computer, laptop, game console, etc. In one embodiment, the sensor 112 may be integrated with computing device 115.

Server 102 includes a software engine that delivers applications, data, program code and other information to networked devices 115, 125 and 130. The software engine of server 102 may perform other processes such as transferring multimedia data, such as audio and video, in a stream of packets that are interpreted and rendered by a software application as the packets arrive. It should be noted that although FIG. 1 shows only two computing devices 115, 125, the system of the present invention supports any number of computing devices connected via network 106.

Server 102, and computing devices 115, 125 may each include program logic comprising computer source code, scripting language code or interpreted language code that perform various functions of the present invention. In one embodiment, the aforementioned program logic may comprise program module 607 in FIG. 6.

FIG. 1 further shows that server 102 includes a database or repository 104, which may be a relational database comprising a Structured Query Language (SQL) database stored in a SQL server. Computing devices 115, 125 may also each include databases. The database 104 may serve data used by server 102, computing devices 115, 125, server 130 and insurance company 140 during the course of operation of the invention.

Environment 100 may be used when computing devices 115, 125, as well as entities 130, 140, transfer data to and from database 104 coupled to server 102. Various types of data may be stored in the database 104 of server 102. For example, the database 104 may store one or more patient records for each patient, i.e., a patient record. A patient record may include personal data for the patient 110, which may include contact information for a patient 110, a medical history of the patient, demographic data of the patient, clinical data of the patient, and psychological data of the patient and occupational data of the patient. A patient record may also include assessment data for the patient, wherein the assessment data includes medical assessment data of the patient, functional assessment data of the patient, psychological assessment data of the patient and economic assessment data of the patient, or the like. A patient record may also include risk data based on the personal data for the patient 110, wherein the risk data defines the patient's risk of further developing a current affliction or having a recurrence of the current affliction, and result data based on the assessment data for the patient, wherein the result data defines a result of the exercise regimen in treating the current affliction.

Additionally, a patient record may also include one or more exercise regimens for a patient, which have been assigned or prescribed by a healthcare professional 120, such as a doctor or physical therapist. An exercise regimen includes a normalized model of at least one exercise activity, wherein the normalized model of the at least one exercise activity may comprise a motion capture sequence that defines the at least one exercise activity. Further, a patient record may also include patient observation data, which pertains to data garnered from observing the patient 110 performing his assigned exercise activities. The patient observation data may include a log of the patient 110 performing the least one exercise activity and patient movement data garnered from a mobile activity sensor attached to the patient. Moreover, a patient record may also include compliance data based on the patient observation data, wherein the compliance data defines the patient's level of compliance with the exercise regimen.

Note that although server 102 is shown as a single and independent entity, in one embodiment of the present invention, the functions of server 102 may be integrated with another entity, such as the computing device 125 and the server 130. Further, server 102 and its functionality, according to a preferred embodiment of the present invention, can be realized in a centralized fashion in one computer system or in a distributed fashion wherein different elements are spread across several interconnected computer systems.

FIG. 1 further shows communications server 130 communicatively coupled with the network 106. The communications server 130 comprises a server having functionality for making telephone calls to the patient 110, in either an automated fashion using an interactive voice response system or via a live operator. The communications server 130 may further comprise a server having email, text and other instant messaging capabilities. FIG. 1 also shows insurance company 140, which may comprise an insurer that provides health related insurance policies covering the cost of medical treatments for patients.

Figure 3:
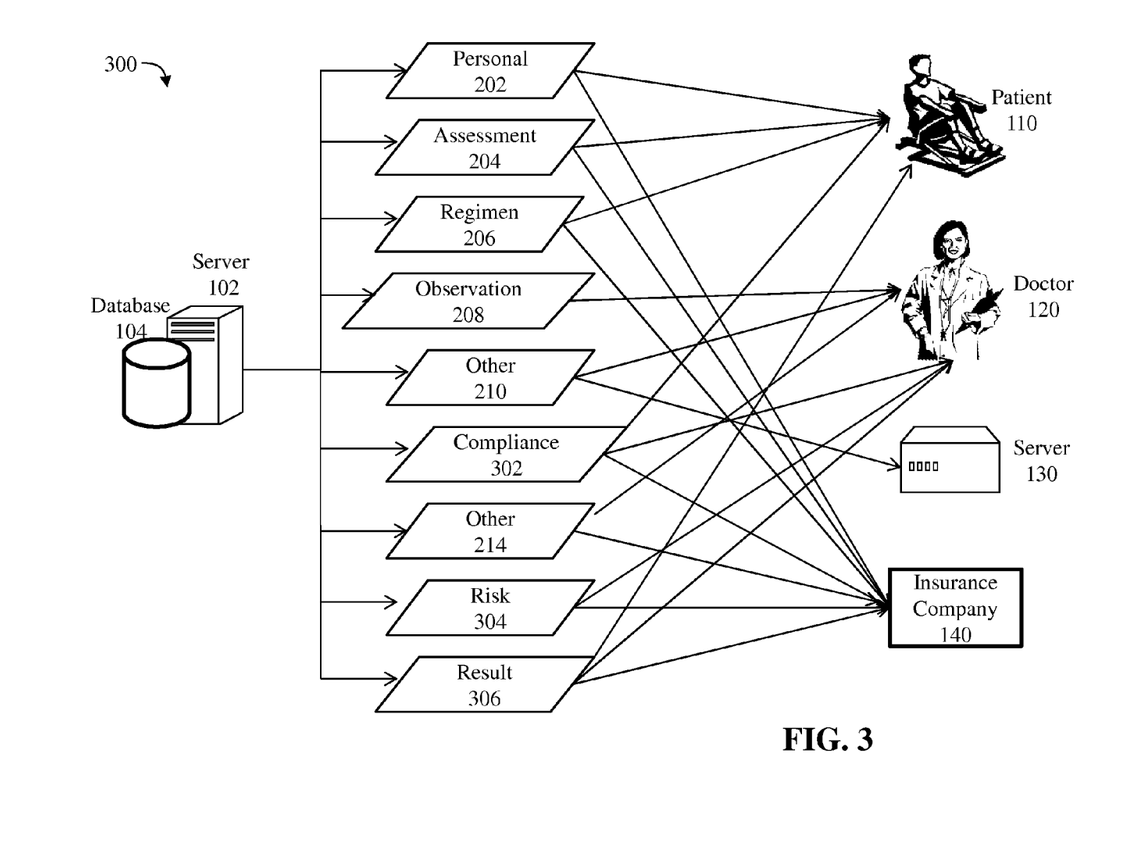
FIG. 3 is a diagram showing an additional data flow of the process for facilitating treatment of patients, according to an example embodiment.
Figure 4:
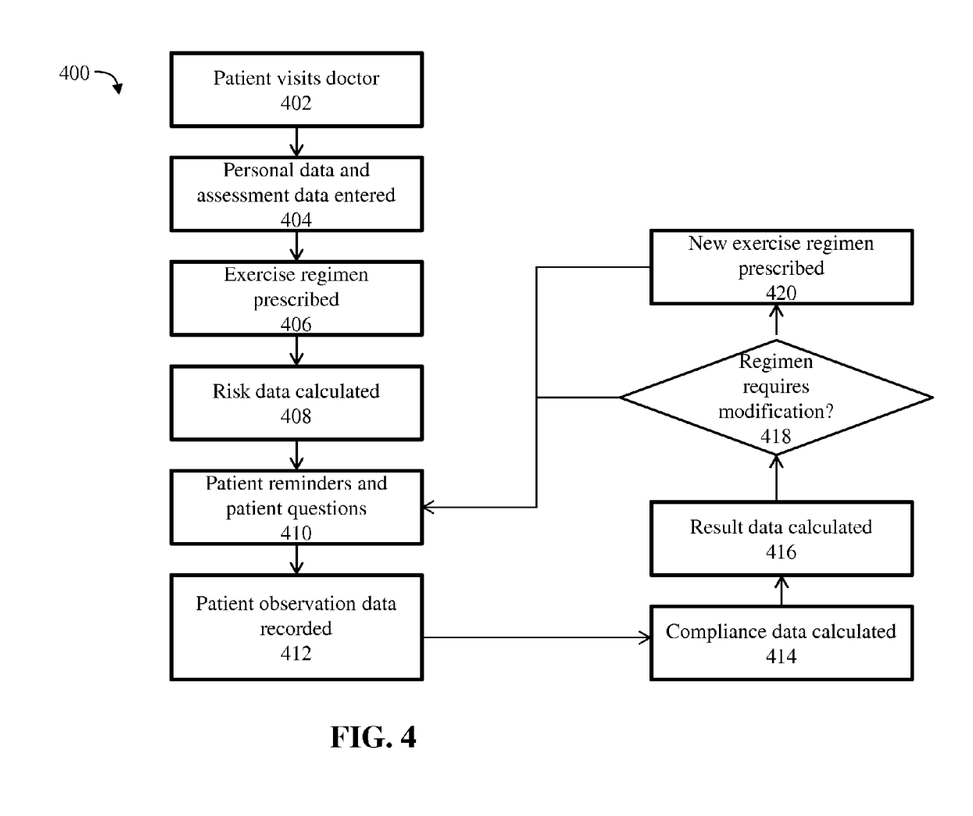
FIG. 4 is a flow chart of a method for facilitating treatment of patients via a server communicatively coupled with a communications network, according to an example embodiment.

FIG. 4 is a flow chart of a method 400 for facilitating treatment of patients via a server 102 communicatively coupled with a communications network 106, according to an example embodiment. Method 400 describes the steps that occur when a patient 110 undergoes treatment by healthcare professional 120 for an affliction, such as chronic pain, wherein the treatment is facilitated by the use of environment 100. The method 400 is described with reference to FIG. 2 and FIG. 3, which are diagrams 200 and 300 showing the data flow of the process for facilitating treatment of patients, according to an example embodiment.

The method 400 begins with the first step 402 wherein a patient 110 may visit a healthcare professional or doctor 120. During the visit, which may be a conventional, in-person visit or a virtual visit using teleconferencing technology, the doctor 120, and/or another healthcare professional working under the direction of the doctor 120, may interact with the patient 110 in order to evaluate the patient medically and establish a treatment plan. During the visit, in step 404, certain information is generated and entered into the database 104 of server 102 as a patient record associated with patient 110.

Figure 2:
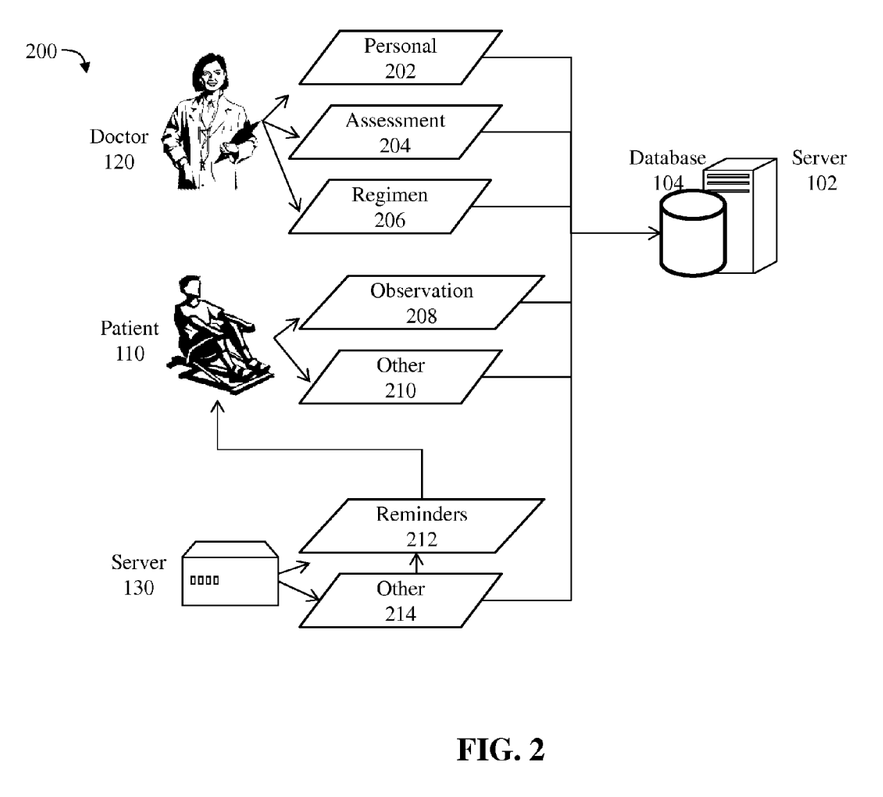
FIG. 2 is a diagram showing the data flow of the process for facilitating treatment of patients, according to an example embodiment.

A patient record may include personal data 202 for the patient 110, which may comprise contact information for a patient 110, a medical history of the patient, demographic data of the patient—such as gender, age, or race—and clinical data of the patient, comprising a record of vital signs, a history of previous episodes of pain or other afflictions, the location of pain or other afflictions, a history of injuries, an obesity evaluation, etc. Personal data 202 may also include psychological data generated during a psychological evaluation of the patient 110, such as the presence of anxiety/depression, self-efficacy measurements, substance abuse history, etc. Personal data 202 may also include occupational data generated during an occupational evaluation, such as employment status, income, educational level, job satisfaction, a description of any lifting or other activity at work (weight, frequency, and duration), the number of days off of work in the last year, etc. FIGS. 2 and 3 show that personal data 202 is entered by the patient 110, doctor 120, or a related entity, into the database 104 and may subsequently be made available to the patient 110 and insurance company 140.

Additionally, a patient record may also include assessment data 204 for the patient 110 that is generated as a result of one or more assessments performed by the doctor 120, and/or another healthcare professional working under the direction of the doctor 120. The assessment data 204 may include medical assessment data of the patient, which may comprise a pain score for a patient experiencing pain, a change or delta of pain score since the last visit, medication side effects experienced by the patient, such as constipation, sedation, nausea/vomiting, etc. The medical assessment data may also include functional assessment data of the patient 110, such as the number of steps per day or distance walked by the patient, the range of motion of various appendages of the patient, the difference in range of motion from expected or adjusted normal values in affected areas, data from a health related quality of life assessment (such as via the SF-12 or SF-36 health survey standards), data from a disease-specific functional questionnaire (such as the Oswestry Disability Index or Roland Morris Disability Questionnaire), a functional score (such as via the International Classification of Functioning (ICF), Disability and Health core sets for certain areas, such as lower back pain), Current Procedural Terminology (CPT) codes, and occupational data, such as employment status, the number days off of work in the last year, absenteeism and diminished productivity at work related to a disease process.

The medical assessment data 204 may also include psychological assessment data of the patient 110, such as a definition of mood trends, patient satisfaction with current health care, self-efficacy and ability to learn long-term treatment strategies, as well as sleep trends, such as the number of hours of sleep per night averaged over last 30 days. The medical assessment data 204 may also include economic assessment data of the patient, including Current Procedural Terminology and International Classification of Diseases (ICD) codes related to episodes of care of the patient, the number of physical therapy visits, the number of emergency room visits, the number of clinic visits, the number of inpatient admission days, and the number of inpatient admission days with a pain-related diagnosis (calculated per year). FIGS. 2 and 3 show that assessment data 204 is entered by the doctor 120, or a related entity, into the database 104 and may subsequently be made available to the patient 110 and insurance company 140.

Based on the personal data 202 and the assessment data 204, in step 406 the doctor 120 may prescribe an exercise regimen to the patient 110. An exercise regimen 206 may include a set of one of more exercise activities that the patient must perform at a given frequency until the next doctor's visit. An exercise regimen 206 may further include a normalized model of at least one exercise activity, wherein the normalized model of the at least one exercise activity may comprise a motion capture sequence that defines the at least one exercise activity. Motion capture describes the process of recording movement of one or more objects or persons. A motion capture sequence may comprise one or more computer files that record actions of a human actor, and uses that information to animate a digital character model in 2D or 3D computer animation. The regimen data 206 may be transmitted to the device 115 of patient 110 and later used by patient 110 when following the prescribed regimen.

FIGS. 2 and 3 show that regimen data 206 is entered by the doctor 120, or a related entity, into the database 104 and may subsequently be made available to the patient 110 and insurance company 140. In one embodiment, the device 125 or server 102 creates the normalized model comprising a motion capture sequence when the doctor 120 performs the at least one prescribed exercise activity in front of a camera of the device 125 or server 102. The exercise regimen 206 is stored in the patient record associated with the patient 110.

In step 408, the server 102 calculates risk data 304 based on the personal data 202 and the assessment data 204 for the patient 110, wherein the risk data 304 defines the patient's risk of further developing a current affliction or having a recurrence of the current affliction. In one embodiment, the step 408 comprises the server 102 calculating a numerical score for the risk data 304 representing the risk of developing a current affliction or having a recurrence of the current affliction. Consequently, the risk data 304 may be used to target patients for early intervention methods, such as education or reminders, to lower the aforementioned risk, as described more fully with respect to the communications server 130. The risk data 304 may also be used to assist with development of pricing strategies for management of patients according to their risk score. FIG. 3 shows that risk data 304 is generated by server 102 and may subsequently be made available to the doctor 120 and insurance company 140.

In one embodiment, the risk data 304 is a numerical value calculated based on a variety of data 202, 204 about the patient. Specifically, points are awarded to the patient in a process that results in a final point count, wherein lower numbers of points (0-9, for example) indicate low risk, middle numbers of points (9-14, for example) indicate moderate risk and higher numbers of points (15-20, for example) are high risk.

Following are various examples of how points may be awarded to a patient in order to calculate risk as a final point score. Females are awarded 2 points, while males are awarded 1 point. Patients aged 25-44 are awarded 2 points, while patients aged 44-65 are awarded 1 point. A first episode of the pain is awarded 1 point, while a second or greater episode is awarded 2 points. Patients with a Body Mass Index (BMI) of normal (18.5-24.99) are awarded zero points, while patients with a BMI of overweight (25-29.9) are awarded 1 point and patients with a BMI of obese (30 and over) are awarded 2 points. Patients with a presence of depression and/or anxiety are awarded 2 points, patients with a previous episode of depression and/or anxiety are awarded 1 point, and patients with no depression and/or anxiety are awarded zero points. Patients scoring 40-60 points on a patient self efficacy questionnaire are awarded zero points, patients scoring 21-39 points on the questionnaire are awarded 1 point and patients scoring 0-20 points are awarded zero points. Patients exhibiting tobacco, alcohol, prescription medication or illicit drug use are awarded 2 points, patients with prior histories of the above are awarded 1 point and patients with no such history are awarded zero points. Patients with up to 3 months of time off work are awarded zero points, patients with 3-6 months off work are awarded 1 point and patients with 6 months to two years off work are awarded 2 points. Patients with a job having heavy lifting or bending are awarded 2 points, patients with a job having light lifting or bending are awarded 1 point and patients with sedentary or office jobs are awarded zero points. Patients having a worker's compensation case or a legal case related to their injury are awarded 2 points, while patients having no such case are awarded no points.

Following is an example of a risk score being applied to an example patient. A patient is enrolled with the following attributes: age 40 (2 pts), gender male (1 pt), second episode of pain (2 points), BMI of 30 (2 points), no known history of depression or anxiety (0 points), questionnaire score of 25 (1 point), and a history of 20 years of smoking 1 pack per day (2 points). The sample patient has been off of work for 2 weeks (0 points), and normally lifts packages frequently at work (2 points). The sample patient has a worker's compensation claim (2 points). Consequently, the sample patient has a risk score of 14. Thus, the patient poses moderate risk of having a poor outcome, thereby indicating a treatment plan requiring greater scrutiny. Also, since greater resources and time will be necessary to address the patient's afflictions, a higher financial commitment would be indicated.

In step 410, the communications server 130 may send the patient 110 exercise regimen reminders 212 (via telephone, text message, email, instant message, etc.) to his mobile sensor 110 or computing device 115. In one embodiment of step 410, the communications server 130 may also send the patient 110 questions (shown as other data 214 in FIG. 2) regarding the patient's treatment. In this embodiment, the patient 110 may provide responses to those questions via the same communications method (shown as other data 210 in FIG. 2). In another embodiment of step 410, the communications server 130 may send the patient 110 exercise regimen reminders and/or questions based on the risk data 304 calculated in step 408 above. Recall the risk data 304 may be used to target patients for early intervention methods, such as education or reminders, to lower the aforementioned risk. FIGS. 2 and 3 shows that reminders 212 and other data 214 are generated by server 130 and may be directly transmitted to the patient 110 (or via server 102). Patient 110 may respond with other data 210 directly to server 130 (or via server 102), wherein other data 210 and 214 may also be provided to doctor 120 and insurance company 140.

In step 412, the computing device 115 may record or keep a log of the patient 110 performing his prescribed exercise regimen. The recorded data comprises patient observation data 208 and may comprises an assessment of the patient 110 performing his prescribed exercise regimen, such as the range of motion of the patient's appendages, the position of the patient's body and the angles achieved by the patient's appendages while performing the exercise activity. In one embodiment, the device 115 executes motion capture processes when the patient 110 performs the at least one prescribed exercise activity in front of a camera of the device 115. The motion capture process may define the range of motion of the patient's appendages, the position of the patient's body and the angles achieved by the patient's appendages while performing the exercise activity. FIGS. 2 and 3 shows that the patient observation data 208 is stored in the patient record associated with the patient 110 in database 104 and may be provided to the doctor 120 and insurance company 140.

In one embodiment of step 412, the patient observation data 208 may include patient movement data and/or patient vital data garnered from the mobile activity sensor 112 attached to the patient 110. In another embodiment of step 412, the doctor 120 may also send the patient 110 questions (similar to other data 214 in FIG. 2) regarding the patient's treatment. In this embodiment, the patient 110 may provide responses to those questions via the same communications method (shown as other data 210 in FIG. 2).

In step 414, the server 102 calculates compliance data 302 based on one or more of the personal data 202, the assessment data 204, the observation data 208, and the other data 210 for the patient 110, wherein the compliance data 302 measures the patient's compliance with the exercise regimen prescribed by the doctor 120. Compliance may be calculated based on how well the patient complied with: 1) the correct form for performing the prescribed exercise activities, 2) the prescribed frequency of the exercise and 3) the correct number of sets and repetitions of the prescribed exercise activities. FIGS. 2 and 3 shows that the compliance data 302 is stored in the patient record associated with the patient 110 in database 104 and may be provided to the patient 110, doctor 120 and insurance company 140.

In one embodiment, the compliance data 302 is an alphanumeric value calculated based on a variety of data 204, 206, 208 about the patient. Specifically, an alphanumeric value is stored based on a patient's adherence to the regimen 206. In one embodiment, a patient is deemed to have strict adherence to the regimen 206 if the patient adhered to the exact regimen, such as performing a walking exercise exactly three times per week for 30 minutes each. In another embodiment, a patient is deemed to have overall adherence to the regimen 206 if the patient adhered to the overall spirit of the regimen. If the regimen, for example, consisted of performing a walking exercise exactly three times per week for 30 minutes each and the patient recorded 90 total, minutes of a walking exercise each week, the patient would be said to exhibit overall adherence or compliance. In another embodiment, a patient is deemed to have exhibited sensor adherence if the patient is shown to have worn the sensor 112 a minimum required amount.

In step 416, the server 102 calculates result data 306 based on one or more of the personal data 202, the assessment data 204, the observation data 208, and the other data 210 for the patient 110, wherein the result data 306 defines a result of the exercise regimen in treating the current affliction of the patient 110. FIGS. 2 and 3 shows that the result data 306 is stored in the patient record associated with the patient 110 in database 104 and may be provided to the patient 110, doctor 120 and insurance company 140. In one embodiment of step 416, the server 102 prepares a report, such as a conventional medical report, that may contain one or more of the result data 306, the personal data 202, the assessment data 204, the regimen data 206, the observation data 208, the other data 210, the compliance data 302, the other data 214 and the risk data 304 for the patient 110.

In one embodiment, the result data 306 may be a numerical or alphanumeric value calculated based on a variety of data 202, 204, 206, 208, 302, 304 about the patient. Specifically, a variety of attributes are considered when calculating the result data 306. Following are various examples of attributes used when calculating risk: a pain score (0-10); a change in pain score over time; lack of opioids being taken by patient; patient taking less than 40 morphine equivalents per day (MED); patient taking 40-120 MED per day; opioid side effects such as constipation, nausea, vomiting and sedation; disease specific and conventional functional measures such as Oswestry Disability Index (ODI) and the Roland Morris Disability Questionnaire scores; objective or sensor-based functional measures such as steps per day recorded by pedometer, range of motion recorded by device 115, and ICF score; ICF score for lower back pain; range of motion in the affected or treated area; Health Related Quality of Life Questionnaire scores; occupational measures such as employment status, number of days off of work in the past year, diminished productivity at work related to disease and questionnaire scores related to absenteeism and presentee-ism; psychological measures such as mood, self efficacy and sleep quantity and quality; health utilization or care process data, such as the number of physical therapy visits per year, the number of emergency room visits per year, the number of physician's office visits per year, the number of in-patient admission days per year, the number of in-patient admission days with a pain related diagnosis per year, the number of interventional procedures per year, the number of surgeries per year, ICD codes, CPR codes and patient satisfaction based on a questionnaire.

After review of the result data 306, the personal data 202, the assessment data 204, the observation data 208, and the other data 210 for the patient 110, doctor 102 may decide that the exercise regimen may require modification. For example, perhaps the patient is not able to perform certain prescribed exercise activities due to a restriction on range of motion of an appendage. In step 418, it is determined whether the exercise regimen requires modification. If the result of the determination of step 418 is positive, then control flows to step 420 where a new exercise regimen is prescribed, similar to the processes described in relation to step 406 above. For example, in step 420, the doctor 120 may prescribe alternative exercise activities that the patient 110 is able to perform, even in the presence of the restriction on range of motion of the patient's appendage. If the result of the determination of step 418 is negative, then control flows back to step 410 where patient reminders and questions are transmitted to the patient 110, and the subsequent processes of steps 412-418 are executed once more.

Figure 5:
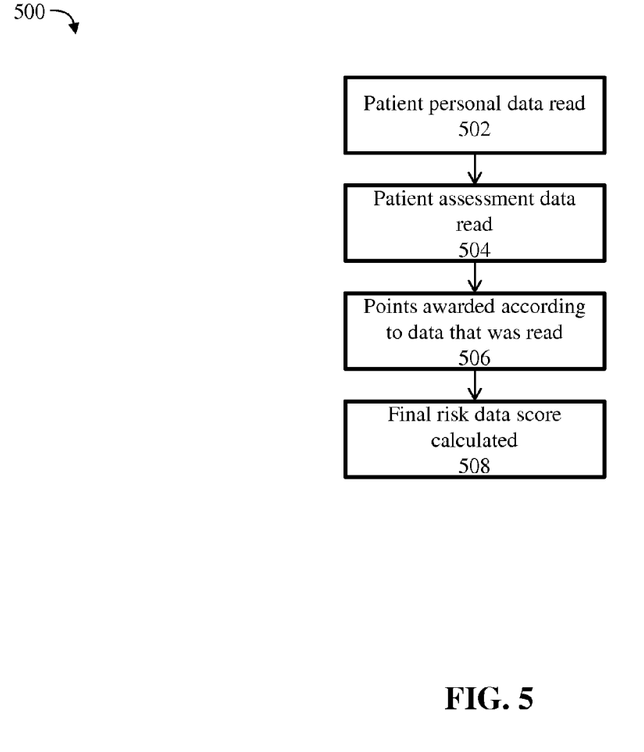
FIG. 5 is a flow chart providing more detail on the processes of calculating risk data, according to an example embodiment.

FIG. 5 is a flow chart providing more detail on the method 500 of calculating risk data 304, according to an example embodiment. Method 500 describes the steps that occur when server 102 calculates a numerical value for risk data 304, as described above with reference to method 400. The method 500 begins with the first step 502 wherein the server 102 reads the patient personal data 202 from the patient record. In step 504 the server 102 reads the patient assessment data 204 from the patient record. In step 506, points are awarded to the patient according to attributes and attribute values read from 202, 204 above, as described with respect to step 408 of FIG. 4 above. In step 508, the final risk data score is calculated based on the points awarded in step 506 above.

Figure 6:
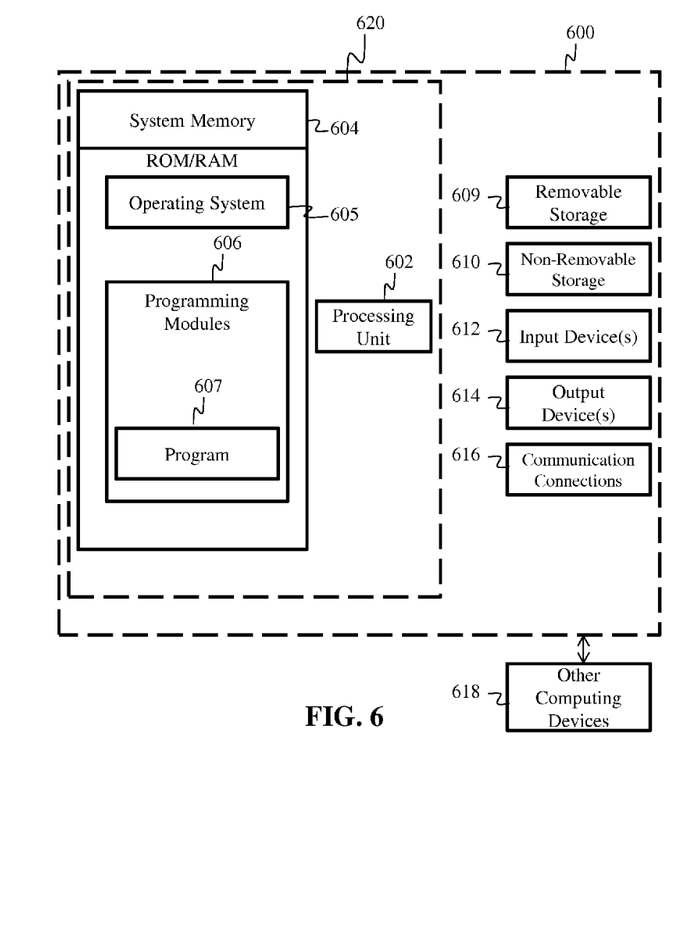
FIG. 6 is a block diagram of a system including a computing device, according to an example embodiment.

FIG. 6 is a block diagram of a system including an example computing device 600 and other computing devices. Consistent with the embodiments described herein, the aforementioned actions performed by servers 102, 130, devices 112, 115, 125 may be implemented in a computing device, such as the computing device 600 of FIG. 6. Any suitable combination of hardware, software, or firmware may be used to implement the computing device 600. The aforementioned system, device, and processors are examples and other systems, devices, and processors may comprise the aforementioned computing device. Furthermore, computing device 600 may comprise an operating environment for method 400 as described above. Method 400 may operate in other environments and is not limited to computing device 600.

With reference to FIG. 6, a system consistent with an embodiment of the invention may include a plurality of computing devices, such as computing device 600. In a basic configuration, computing device 600 may include at least one processing unit 602 and a system memory 604. Depending on the configuration and type of computing device, system memory 604 may comprise, but is not limited to, volatile (e.g. random access memory (RAM)), non-volatile (e.g. read-only memory (ROM)), flash memory, or any combination or memory. System memory 604 may include operating system 605, and one or more programming modules 606. Operating system 605, for example, may be suitable for controlling computing device 600's operation. In one embodiment, programming modules 606 may include, for example, a program module 607 for executing the actions of servers 102, 130, devices 112, 115, 125. Furthermore, embodiments of the invention may be practiced in conjunction with a graphics library, other operating systems, or any other application program and is not limited to any particular application or system. This basic configuration is illustrated in FIG. 6 by those components within a dashed line 620.

Computing device 600 may have additional features or functionality. For example, computing device 600 may also include additional data storage devices (removable and/or non-removable) such as, for example, magnetic disks, optical disks, or tape. Such additional storage is illustrated in FIG. 6 by a removable storage 609 and a non-removable storage 610. Computer storage media may include volatile and nonvolatile, removable and non-removable media implemented in any method or technology for storage of information, such as computer readable instructions, data structures, program modules, or other data. System memory 604, removable storage 609, and non-removable storage 610 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 600. Any such computer storage media may be part of device 600. Computing device 600 may also have input device(s) 612 such as a keyboard, a mouse, a pen, a sound input device, a camera, a touch input device, etc. Output device(s) 614 such as a display, speakers, a printer, etc. may also be included. The aforementioned devices are only examples, and other devices may be added or substituted.

Computing device 600 may also contain a communication connection 616 that may allow device 600 to communicate with other computing devices 618, such as over a network in a distributed computing environment, for example, an intranet or the Internet. Communication connection 616 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 604, including operating system 605. While executing on processing unit 602, programming modules 606 (e.g. program module 607) may perform processes including, for example, one or more of method 400's stages as described above. The aforementioned processes are examples, and processing unit 602 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable consumer electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods' stages may be modified in any manner, including by reordering stages and/or inserting or deleting stages, without departing from the invention.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method on a server for facilitating treatment of patients, wherein the server is communicatively coupled to a communications network, comprising:

receiving, via the communications network, an exercise regimen for a patient, wherein the exercise regimen includes a) a prescribed frequency of at least one exercise activity, b) a number of sets and repetitions of the at least one exercise activity, and b) a normalized model of the at least one exercise activity, wherein the normalized model of the at least one exercise activity comprises a motion capture sequence that defines the at least one activity;

transmitting, via the communications network, the exercise regimen to a computing device of the patient;

receiving, via the communications network, patient observation data, including a log of the patient performing the least one exercise activity;

generating compliance data based on the patient observation data, wherein the compliance data defines the patient's level of compliance with the exercise regimen, and wherein the compliance data includes 1) whether the patient used correct form in performing the at least one activity, 2) whether the patient met the prescribed frequency of the at least one exercise activity, and 3) whether the patient performed the number of sets and repetitions of the at least one exercise activity; and generating a report including identifying data about the patient, medical and functional assessment data of the patient, the exercise regimen data, the compliance data and the patient observation data.

2. The method of claim 1, wherein the normalized model of the at least one exercise activity comprises a motion capture sequence that defines the at least one activity, and wherein the motion capture sequence comprises multiple computer files.

3. The method of claim 2, wherein the step of receiving patient observation data further comprises:
receiving, via the communications network, patient observation data, including: 1) a log of the patient performing the least one exercise activity and 2) patient movement data and/or patient vital data garnered from a mobile activity sensor attached to the patient.

4. The method of claim 3, further comprising:
receiving, via the communications network, personal data for the patient, wherein the personal data includes demographic data of the patient, clinical data of the patient, psychological data of the patient and occupational data of the patient.

5. The method of claim 4, further comprising:
generating risk data based on the personal data for the patient, wherein the risk data defines the patient's risk of further developing a current affliction or having a recurrence of the current affliction.

6. The method of claim 5, further comprising:
receiving, via the communications network, assessment data for the patient, wherein the assessment data includes medical assessment data of the patient, functional assessment data of the patient, psychological assessment data of the patient and economic assessment data of the patient.

7. The method of claim 6, further comprising:
generating result data based on the assessment data for the patient, wherein the result data defines a result of the exercise regimen in treating the current affliction.

8. A method on a server for facilitating treatment of patients, wherein the server is communicatively coupled to a communications network, comprising:
receiving, via the communications network, an exercise regimen for a patient, wherein the exercise regimen includes a) a prescribed frequency of at least one exercise activity, b) a number of sets and repetitions of the at least one exercise activity, and b) a normalized model of the at least one exercise activity, wherein the normalized model of the at least one exercise activity comprises a motion capture sequence that defines the at least one activity;
transmitting, via the communications network, the exercise regimen to a computing device of the patient;
receiving, via the communications network, patient observation data, including a log of the patient performing the least one exercise activity;
generating compliance data based on the patient observation data, wherein the compliance data defines the patient's level of compliance with the exercise regimen, and wherein the compliance data includes 1) whether the patient used correct form in performing the at least one activity, 2) whether the patient met the prescribed frequency of the at least one exercise activity, and 3) wherein the patient performed the number of sets and repetitions of the at least one exercise activity; and
generating a report including identifying data about the patient, medical and functional assessment data of the patient, the exercise regimen data, the patient observation data and the compliance data.

9. The method of claim 8, wherein the normalized model of the at least one exercise activity comprises a motion capture sequence that defines the at least one activity, and wherein the motion capture sequence comprises multiple computer files.

10. The method of claim 9, wherein the step of receiving patient observation data further comprises:
receiving, via the communications network, patient observation data, including: 1) a log of the patient performing the least one exercise activity and 2) patient movement data and/or patient vital data garnered from a mobile activity sensor attached to the patient.

11. The method of claim 10, further comprising:
receiving, via the communications network, personal data for the patient, wherein the personal data includes demographic data of the patient, clinical data of the patient, psychological data of the patient and occupational data of the patient.

12. The method of claim 11, further comprising:
generating risk data based on the personal data for the patient, wherein the risk data defines the patient's risk of further developing a current affliction or having a recurrence of the current affliction.

13. The method of claim 12, further comprising:
receiving, via the communications network, assessment data for the patient, wherein the assessment data includes medical assessment data of the patient, functional assessment data of the patient, psychological assessment data of the patient and economic assessment data of the patient.

14. The method of claim 13, further comprising:
generating result data based on the assessment data for the patient, wherein the result data defines a result of the exercise regimen in treating the current affliction.

15. A method on a server for facilitating treatment of patients, wherein the server is communicatively coupled to a communications network, comprising:
receiving, via the communications network, an exercise regimen for a patient, wherein the exercise regimen includes a) a prescribed frequency of at least one exercise activity, b) a number of sets and repetitions of the at least one exercise activity, and b) a normalized model of the at least one exercise activity, wherein the normalized model of the at least one exercise activity comprises a motion capture sequence that defines the at least one activity;
transmitting, via the communications network, the exercise regimen to a computing device of the patient;
receiving, via the communications network, patient observation data, including: 1) a log of the patient performing the least one exercise activity and 2) patient movement data garnered from a mobile activity sensor attached to the patient;
generating compliance data based on the patient observation data, wherein the compliance data defines the patient's level of compliance with the exercise regimen, and wherein the compliance data includes 1) whether the patient used correct form in performing the at least one activity, 2) whether the patient met the prescribed frequency of the at least one exercise activity, and 3) whether the patient performed the number of sets and repetitions of the at least one exercise activity; and
generating a report including identifying data about the patient, medical and functional assessment data of the patient, the exercise regimen data, the patient observation data, the patient movement data and the compliance data.

16. The method of claim 15, wherein the normalized model of the at least one exercise activity comprises a motion capture sequence that defines the at least one activity, and wherein the motion capture sequence comprises multiple computer files.

17. The method of claim 16, wherein the step of receiving patient observation data further comprises:

receiving, via the communications network, patient observation data, including: 1) a log of the patient performing the least one exercise activity and 2) patient movement data and/or patient vital data garnered from a mobile activity sensor attached to the patient.

18. The method of claim 17, further comprising:
receiving, via the communications network, personal data for the patient, wherein the personal data includes demographic data of the patient, clinical data of the patient, psychological data of the patient and occupational data of the patient.

19. The method of claim 18, further comprising:
generating risk data based on the personal data for the patient, wherein the risk data defines the patient's risk of further developing a current affliction or having a recurrence of the current affliction.

* * * * *